United States Patent
Kuehner et al.

(10) Patent No.: US 9,622,815 B2
(45) Date of Patent: Apr. 18, 2017

(54) ELECTRODE DEVICE OF AN ELECTROSURGICAL INSTRUMENT

(75) Inventors: Ralf Kuehner, Stuttgart (DE); Dietmar Karwei, Ofterdingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 35 days.

(21) Appl. No.: 13/882,675

(22) PCT Filed: Nov. 4, 2011

(86) PCT No.: PCT/EP2011/069435
§ 371 (c)(1),
(2), (4) Date: Apr. 30, 2013

(87) PCT Pub. No.: WO2012/059587
PCT Pub. Date: May 10, 2012

(65) Prior Publication Data
US 2013/0226176 A1 Aug. 29, 2013

(30) Foreign Application Priority Data
Nov. 4, 2010 (DE) .......... 10 2010 060 336

(51) Int. Cl.
*A61B 18/18* (2006.01)
*A61B 17/3203* (2006.01)
(Continued)

(52) U.S. Cl.
CPC .......... *A61B 18/18* (2013.01); *A61B 17/3203* (2013.01); *A61B 18/042* (2013.01);
(Continued)

(58) Field of Classification Search
CPC ........... A61B 2017/0088; A61N 1/042; A61N 1/0436; B28B 11/0845
(Continued)

(56) References Cited

U.S. PATENT DOCUMENTS 4,503,855 A * 3/1985 Maslanka .............. A61B 18/14
606/47
4,850,353 A * 7/1989 Stasz .................. A61B 18/1402
606/39
(Continued)

FOREIGN PATENT DOCUMENTS

CN 101687213 A 3/2010
CN 101460110 B 3/2011
(Continued)

OTHER PUBLICATIONS

JA Spadaro, TJ Berger, SD Barranco, SE Chapin, RO Becker. Antibacterial Effects of Silver Electrodes with Weak Direct Current. Antimicrobial Agents and Chemotherapy, Nov. 1974, vol. 6, No. 5, p. 637-642.*

(Continued)

*Primary Examiner* — Ronald Hupczey, Jr.
*Assistant Examiner* — Bo Ouyang
(74) *Attorney, Agent, or Firm* — Fitch, Even, Tabin & Flannery LLP

(57) ABSTRACT

An electrode device of an electrosurgical instrument is known, comprising at least one electrically conductive electrode section and an electrically insulating carrier section, wherein both the electrode section and the carrier section are made from a ceramic material. In order to improve the mechanical and electrical properties and in order to simplify the production, a green body of the carrier section and a green body of the electrode section are connected to each other, in particular materially, to form a single composite green body and are jointly sintered.

5 Claims, 1 Drawing Sheet

(51) Int. Cl.
  *A61B 18/04* (2006.01)
  *A61B 18/14* (2006.01)
  *H05K 3/00* (2006.01)
  *A61B 17/00* (2006.01)
  *A61B 18/00* (2006.01)

(52) U.S. Cl.
  CPC ....... *A61B 18/1402* (2013.01); *H05K 3/0067* (2013.01); *A61B 2017/0088* (2013.01); *A61B 2017/00526* (2013.01); *A61B 2018/00148* (2013.01)

(58) Field of Classification Search
  USPC .......................................... 264/69, 614–617
  See application file for complete search history.

(56) References Cited

U.S. PATENT DOCUMENTS

| | | | |
|---|---|---|---|
| 4,862,890 | A | 9/1989 | Stasz et al. |
| 4,961,757 | A * | 10/1990 | Rhodes ................ B23B 27/148 501/128 |
| 5,505,729 | A | 4/1996 | Rau |
| 5,665,085 | A | 9/1997 | Nardella |
| 5,925,039 | A * | 7/1999 | Landingham .................. 606/41 |
| 6,146,581 | A * | 11/2000 | Bitz et al. ........................ 419/5 |
| 6,277,114 | B1 * | 8/2001 | Bullivant et al. ............... 606/41 |
| 6,584,349 | B1 * | 6/2003 | Sage et al. ...................... 604/20 |
| 7,837,683 | B2 * | 11/2010 | Carmel et al. .................. 606/41 |
| 8,409,656 | B2 | 4/2013 | Bay et al. |
| 2004/0111087 | A1 * | 6/2004 | Stern ...................... A61B 18/14 606/41 |
| 2005/0171526 | A1 | 8/2005 | Rioux et al. |
| 2006/0163774 | A1 * | 7/2006 | Abels et al. ................... 264/293 |
| 2007/0075451 | A1 * | 4/2007 | Winter et al. ................. 264/126 |
| 2007/0123853 | A1 * | 5/2007 | Nesbitt ........................... 606/45 |
| 2007/0173872 | A1 | 7/2007 | Neuenfeldt |
| 2008/0188845 | A1 | 8/2008 | McGreevy et al. |
| 2010/0087814 | A1 | 4/2010 | Desinger et al. |

FOREIGN PATENT DOCUMENTS

| | | |
|---|---|---|
| DE | 19652098 A1 | 6/1998 |
| EP | 0998879 A1 | 5/2000 |
| EP | 1293169 A1 | 3/2003 |
| EP | 2042112 A2 | 4/2009 |
| JP | H01288291 A | 11/1989 |
| JP | H0263449 A | 3/1990 |
| KR | 2004-0013236 | 2/2004 |
| WO | 9940858 A1 | 8/1999 |
| WO | 2010118818 A1 | 10/2010 |

OTHER PUBLICATIONS

GL Hornyak, JJ Moore, HF Tibbals, J Dutta. Fundamentals of Nanotechnology. 2008, CRC Press, p. 464.*
English translation of Office Action from corresponding Russian Application No. 2013125573/20(037684) dated Jul. 16, 2014, 8 pages.
English Translation of Korean Office Action for corresponding Korean Application No. 2013-7011405, dated Jun. 29, 2015, 7 pages.
Office action in corresponding Chinese Application No. 201180053350.9, dated Mar. 13, 2015, 8 pages.
English translation of Office action in corresponding Korean application No. 2013-7011405, dated Jan. 25, 2016, 6 pages.
Japanese Search Report in corresponding Japanese application No. 2013-537150, dated Aug. 11, 2015, 15 pages.
Chinese Office Action in corresponding Chinese application No. 201180053350.9, dated Oct. 18, 2015, 13 pages.

* cited by examiner

ELECTRODE DEVICE OF AN ELECTROSURGICAL INSTRUMENT

CROSS REFERENCE TO RELATED APPLICATIONS

This patent application is the national phase of PCT/EP2011/069435, filed Nov. 4, 2011, which claims the benefit of German Patent Application No. DE 102010060336.8 filed Nov. 4, 2010, the contents of each which are incorporated herein by reference in their entireties.

TECHNICAL FIELD

The invention relates to an electrode device of an electrosurgical instrument.

BACKGROUND

In surgery, frequently instruments are used that can cut and coagulate tissue with the aid of radio-frequency (RF) current. In many instances such instruments are made of stainless steel; however, it is possible that tissue or the resultant substances will build up on the instrument. Cleaning of the instrument is laborious.

In order to avoid or at least minimize such a buildup, publication U.S. Pat. No. 5,925,039 suggested that a metal carrier be coated with a conductive ceramic. However, such instruments display only relatively little durability because the highly different coefficients of expansion of ceramic and metal carrier result in the chipping of the coating when the instrument is heated.

Publication U.S. Pat. No. 4,862,890 discloses an electrode device wherein a metal coating is applied to a ceramic carrier. Due to the elasticity of the metal coating, the aforementioned tension problems are not as distinct when the electrode is heated; however, again, a buildup occurs relatively easily.

Publication U.S. Pat. No. 5,665,085 discloses an electrode device, wherein an insulating ceramic comprising a conductive ceramic coating is suggested. The production of this electrode device or the electrosurgical instrument provided therewith is laborious and durability is not adequate.

SUMMARY

Therefore, the object of the invention is to develop an electrode device of the aforementioned type such that increased durability is achieved with simplified production.

In one approach, an electrode device of an electrosurgical instrument including at least one conductive electrode section and one electrically insulating carrier section, wherein the electrode section, like the carrier section, is made of a ceramic material, in that a green body of the carrier section and a green body of the electrode section are connected to each other, in particular materially, to form a single composite green body and are jointly sintered.

Therefore, an essential feature of the invention is that the two ceramic materials are combined already in the green body state and thus have boundary surfaces that transition into each other, before they are jointly sintered. This manufacturing technique is quite obvious when viewed in a sectional view, and the device can be quite well distinguished from the so far common electrode devices.

The electrode section and the carrier section are preferably made of ceramic material exhibiting essentially the same coefficient of thermal expansion. As a result of this, a body is formed that is insensitive to temperature fluctuations. Preferably, the ceramic material in both cases is silicon nitride, however, with a different doping or admixing with constituents generating a conductivity, said constituents being generally known. In particular, admixing constituents may include aluminum oxide, yttrium oxide or magnesium oxide.

Prior to being sintered, the composite green body is preferably subjected to a surface treatment, in particular, by means of a laser or by mechanical cutting, e.g., by slide grinding. This results in excellent surface structures due to the softness of the green body.

In a preferred embodiment of the invention the electrode section is connected to the carrier section with the formation of undercuts, thus increasing the stability of the device and simplifying the production of the composite green body, and also stabilizing the composite green body.

Due to the conductivity of the ceramic that is being used, the electrode section can be used without further treatment. In alternative embodiments of the invention, however, the electrode section is at least partially coated, in particular, metallized or electroplated. As a result of this, e.g., those sections of the electrode section that are electrically connected to supply wires can be imparted with a particularly low transition resistance.

Furthermore, the aforementioned object is achieved with a method for the production of an electrode device of an electrosurgical instruments, comprising the following steps:
a) Making available an electrically insulating first ceramic material;
b) Making available an electrically conductive second ceramic material;
c) Producing a composite green body comprising at least one carrier section of the first ceramic material and at least one electrode section of the second ceramic material;
d) Joint sintering of the first and the second ceramic materials, said materials together forming the composite green body.

By combining the two green bodies in one single composite green body and by subsequent sintering, a particularly stable structure is achieved in a simple manner.

Prior to sintering, the green body is preferably subjected to a surface treatment, in particular with a laser or by mechanical cutting, e.g., slide grinding. Consequently, it is possible to achieve high-quality surfaces and also extremely fine structures in a simple manner.

Advantageously, the first and the second ceramic materials exhibit essentially the same coefficients of thermal expansion; in particular, they comprise the same ceramic material, i.e., in particular silicon nitride, wherein, however, a different doping or admixing with constituents is used that impart conductivity. As a result of this, highly stable and temperature-insensitive instruments can be produced.

The production is particularly simple and functionally reliable when the composite green body is produced by means of a 2K injection molding process (two-component injection molding process) by means of a production method that has been known per se.

At this point it should be emphasized that a plurality of ceramics can be used if it is only necessary to ensure that the conductive, as well as the non-conductive, ceramic exhibit at least highly similar coefficients of thermal expansion.

A particularly advantageous use of electrode devices configured or produced in this manner is that they are used as part of an electrosurgical cutting and/or coagulation tool, in which case the electrode section comes into direct contact with the tissue to be treated. Hardly any buildup can be observed on such electrode devices.

Another advantageous use is the configuration of a preparation instrument, wherein the carrier section is configured, in particular, as a hook-shaped, spherical or semi-spherical, or disk-shaped preparation section, and the electrode section forms a cutting or coagulation section of the preparation instrument.

Another advantageous application is that the electrode device can be used in a water jet surgical instrument, wherein the carrier section comprises a lumen for the passage of a cutting fluid and the electrode device is used for electrosurgical cutting or coagulation.

Alternatively, or also additionally, a use in a plasma surgical instrument is possible, wherein the electrode section is preferably disposed as a perfusable ionization electrode.

Overall, all the aforementioned instruments or electrode devices can be used in endoscopic surgical instruments in an advantageous manner because miniaturization is highly possible.

BRIEF DESCRIPTION OF THE DRAWINGS

Hereinafter the invention will be explained with reference to drawings. They show in FIG. 1 a partial sectional view of a spatula-shaped electrosurgical instrument, FIG. 2 a non-sectional view of the instrument as in FIG. 1, FIG. 3 the spatula section of the instrument as in FIGS. 1 and 2, i.e., during a first production step, FIG. 4 a sectional view along line A-A of FIG. 3, FIG. 5 a schematic representation of the instrument as in FIGS. 1 through 4, during a second production step.

In the description hereinafter, the same reference signs are used for the same parts or for parts having the same function.

DETAILED DESCRIPTION

Figure 1:
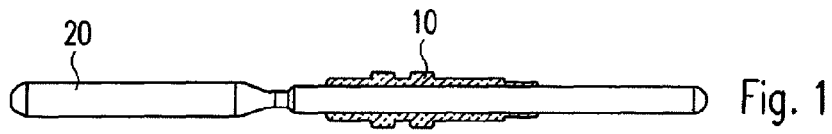
Figure 2:
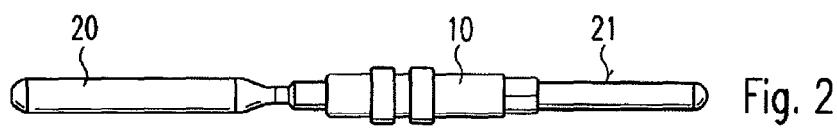

FIGS. 1 and 2 show a spatula-shaped electrosurgical instrument as is generally being used. In this case, a carrier section 10 is applied to an electrode section 20. The carrier section 10 is insulating, whereas the electrode section 20 is electrically conductive. In both cases, a silicon nitride ceramic is used, wherein the silicon nitride of the electrically conductive electrode section 20 is doped with aluminum oxide, yttrium oxide and magnesium oxide. This doping has the effect that the coefficient of expansion remains virtually the same with respect to undoped silicon nitride, that, however, the electrical conductivity is at least good enough that a use as an electrode is easily possible.

The connector section downstream of the carrier section 10, said connector being used for inserting the instrument in a standard grip, has a coating 21 of metal to ensure the lowest-possible transition resistance to the connecting elements.

Hereinafter, the use of the spatula-shaped electrosurgical instrument in accordance with FIGS. 1 and 2 will be explained.

Figure 3:
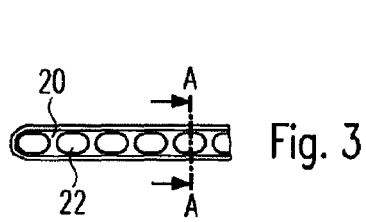
Figure 4:
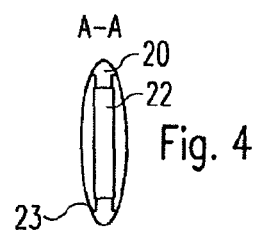
Figure 5:
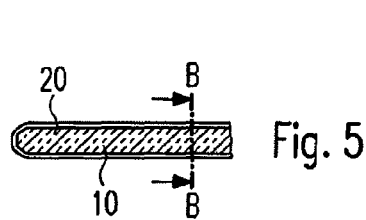
Figure 6:
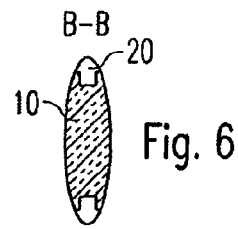
FIG. 6 a sectional view along line B-B of FIG. 5.

First, a green body is produced of electrically conductive silicon nitride material, said green body having the form shown in FIGS. 3 and 4. This green body is provided with openings 22, as well as with undercuts 23. In a next step, non-conductive silicon nitride is injection molded to the green body in accordance with FIGS. 3 and 4 by a 2K process, so that the openings 22 and the undercuts 23 are filled. The thusly produced "composite green body" consists of partially doped and partially non-doped silicon nitride, thus comprises electrode sections 20 and carrier sections 10. Subsequently to this injection molding process, the composite green body is fired or sintered the manner known per se so that an extremely stable object—as shown by FIGS. 1 and 2—is obtained. The stability is particularly high because the boundary surfaces between the conductive and the non-conductive silicon nitride are "blurred" and can virtually no longer be detected due to the low dope amounts in a micrograph or a sectional view. Consequently, it is also possible to distinguish an inventive electrosurgical instrument from an instrument, wherein an electrically conductive ceramic was applied to a non-conductive silicon ceramic body.

At this point it shall be pointed out again that, of course, silicon nitride is not the only ceramic that is suitable for the production of instruments in accordance with the invention or for performing the method in accordance with the invention. Regarding this, relevant literature provides numerous additional examples.

Figure 7:
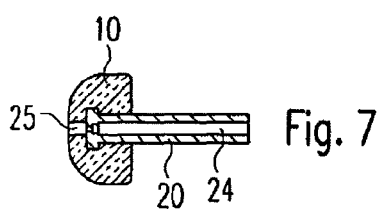
FIG. 7 a longitudinal section of an end section of another electrosurgical instrument, FIG. 8 a longitudinal section of another embodiment of the invention of an electrosurgical instrument, FIG. 9 a plan view of the instrument as in FIG. 8, and FIG. 10 a longitudinal section of the end section of grasping forceps in accordance with one embodiment of the invention.
Figure 8:
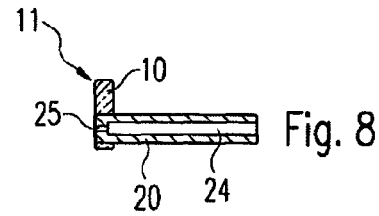
Figure 9:

In the embodiments of the invention shown by FIGS. 7, 8 and 9 herein, the end sections of an electrosurgical instrument are depicted. Each of these has a tubular body that is made of electrically conductive silicon nitride and forms an electrode section 20, said electrode section comprising a lumen 24 and a nozzle 25 at its end. In doing so, a device for fluid jet surgery (water jet surgery) can be produced. With the aid of the above-described method, the end of the electrode section 20 is configured as a semi-spherical carrier section 10 (FIG. 7) or a hook 11 (FIGS. 8 and 9), each being usable for the preparation of tissue. The instruments shown by FIGS. 7 through 9 thus feature three possibilities for use. Firstly, the instrument can be mechanically finished; secondly, the tissue can be separated by means of a water jet; and, thirdly, cutting and coagulation procedures can be performed with the aid of radio-frequency currents.

Figure 10:
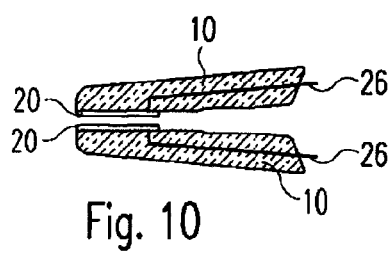

The embodiment of the invention shown by FIG. 10 is the end section (in longitudinal section) of grasping forceps. In this case, the two jaws of the grasping forceps are configured as the carrier bodies 10; and it is only on the end sections where the electrode sections 20 of conductive silicon nitride ceramic are applied to the non-conductive silicon nitride ceramic. In this case, contacting is achieved via lines 26 that are extrusion coated during the production of the composite green body.

The surfaces of the electrically conductive electrode sections 20 may be polished or fluted, in which case such a method step of a surface treatment is preferably performed on the composite green body.

LIST OF REFERENCE SIGNS

10 Carrier section
11 Hook
20 Electrode section

21 Metallization
22 Opening
23 Undercut
24 Lumen
25 Nozzle
26 Line

The invention claimed is:

1. An electrode device of an electrosurgical instrument, the electrode device comprising:
   at least one conductive electrode section made of a first ceramic material; and
   an electrically insulating carrier section connected to the at least one conductive electrode section and made of a second ceramic material;
   wherein the first ceramic material and the second ceramic material are stably connected having a blurred boundary surface caused by being jointly sintered;
   wherein the first ceramic material and the second ceramic material comprise a same base ceramic material, exhibit essentially same coefficients of thermal expansion, and have different doping of constituents to generate different electrical conductivities;
   wherein the same base ceramic material comprises silicon nitride.

2. The electrode device of claim 1 wherein the first ceramic material contains at least one of aluminum oxide, yttrium oxide, or magnesium oxide as doping constituents.

3. The electrode device as in claim 1 wherein the conductive electrode section and the electrically insulating carrier section have a fine surface structure resulting from subjecting the first ceramic material and the second ceramic material to a surface treatment comprising one of by laser or by mechanical cutting prior to being jointly sintered.

4. The electrode device as in claim 1 wherein the electrode section is interlocked with the carrier section via undercuts.

5. The electrode device as in claim 1 wherein the electrode section is at least partially metallized.

* * * * *